United States Patent [19]
Dias Nahoum

[11] Patent Number: 5,952,361
[45] Date of Patent: Sep. 14, 1999

[54] COMPOSITIONS

[76] Inventor: Cesar Roberto Dias Nahoum, P.O. Box 1539, King of Prussia, Pa. 19406-0939

[21] Appl. No.: 09/037,097

[22] Filed: Mar. 9, 1998

Related U.S. Application Data

[62] Division of application No. 08/444,130, May 18, 1995, Pat. No. 5,773,457, which is a continuation of application No. 08/381,945, Feb. 15, 1995.

[30] Foreign Application Priority Data

Aug. 21, 1992 [BR] Brazil ..................... 9203277

[51] Int. Cl.$^6$ .................. A61K 31/415
[52] U.S. Cl. ............ 514/396; 514/397; 514/401; 514/402; 514/579; 514/947; 514/929
[58] Field of Search .................... 514/396, 397, 514/401, 402, 579, 947, 929

[56] References Cited

U.S. PATENT DOCUMENTS

| | | |
|---|---|---|
| 3,636,225 | 1/1972 | Fassel . |
| 4,013,659 | 3/1977 | Durant et al. ................ 424/263 |
| 4,126,670 | 11/1978 | Durant et al. ................ 424/9 |
| 4,127,118 | 11/1978 | Latorre . |
| 4,311,707 | 1/1982 | Birnbaum et al. . |
| 4,472,376 | 9/1984 | Kamishita . |
| 4,521,421 | 6/1985 | Foreman . |
| 4,532,135 | 7/1985 | Edwards . |
| 4,801,587 | 1/1989 | Voss et al. . |
| 4,840,952 | 6/1989 | Gamble et al. . |
| 4,863,911 | 9/1989 | Anderson et al. . |
| 4,931,445 | 6/1990 | Goldstein et al. . |
| 5,059,603 | 10/1991 | Rubin . |
| 5,145,852 | 9/1992 | Virag . |
| 5,147,855 | 9/1992 | Gozes et al. . |
| 5,177,070 | 1/1993 | Katz . |
| 5,190,967 | 3/1993 | Riley . |
| 5,192,806 | 3/1993 | Pill et al. . |
| 5,214,030 | 5/1993 | Stief . |
| 5,242,391 | 9/1993 | Place et al. . |
| 5,256,652 | 10/1993 | El-Rashidy . |
| 5,270,323 | 12/1993 | Milne et al. . |
| 5,336,678 | 8/1994 | Cavallini . |
| 5,474,535 | 12/1995 | Place et al. . |
| 5,565,466 | 10/1996 | Gioco et al. . |

FOREIGN PATENT DOCUMENTS

| | | |
|---|---|---|
| 0 266 968 A2 | 10/1988 | European Pat. Off. . |
| 0 346 297 A1 | 5/1989 | European Pat. Off. . |
| 0 432 199 B1 | 9/1989 | European Pat. Off. . |
| 0 357 581 A1 | 6/1990 | European Pat. Off. . |
| 0 357 581 B1 | 6/1990 | European Pat. Off. . |
| 0 459 377 A2 | 5/1991 | European Pat. Off. . |

OTHER PUBLICATIONS

Kim et al., Journal of Urology, 153(2), pp. 506–510 (1995).

*Primary Examiner*—James H. Reamer
*Attorney, Agent, or Firm*—Dara L. Dinner; Stephen Venetianer; Charles M. Kinzig

[57] ABSTRACT

The present invention involves the novel use of various classes of drugs, such as $H_2$ and $H_3$ agonists, as erectogenic agents in the treatment of male and female sexual dysfunction.

34 Claims, 2 Drawing Sheets

COMPOSITIONS

RELATED APPLICATIONS

This application is a divisional of U.S. Ser. No. 08/444,130, filed May 18, 1995, now U.S. Pat. No. 5,773,457, which is a continuation of U.S. Ser. No. 08/381,945, filed Feb. 15, 1995.

FIELD OF THE INVENTION

The present invention involves the novel use of various classes of drugs, such as $H_2$ agonists, as erectogenic agents in the treatment of erectile dysfunction.

BACKGROUND OF THE INVENTION

The year 1982 marked the beginning of a new era in the diagnosis and treatment of male sexual impotence. At that time, the new development was the use of papavetine as a drug which, when injected intracavernously, was capable of inducing a penile erection in humans, Virag, R. "Intracavernous injection of papaverine for erectile failure". *Lancet* 2: 938 (1982).

Regrettably, universal medical experience with this drug over several years revealed the severity of some of its side-effects, Jünemann, K. P. and Alken, P. "Pharmacotherapy of erectile dysfunction; a review". *Int. J. Impotence Res.* 1, 71–93 (1988). A major disadvantage of papaverine was the occurrence of unduly prolonged erection with the danger of priapism. Papaverine was also tried in combination with the alpha sympathetic blocker phentolamine, Zorgniotti, A. W. and Lefleur, R. S. *J. Urol.,* 133(1): 39–41, (1985). Phenoxybenzamine, another alpha-adrenergic blocker was also tested, Brindley, G. S. *Br. J, Psychiatry,* 143: 332–337 (1983). The use of phenoxybenzamine for the management of impotence was abandoned at this time because of evidence obtained from experiments with animals suggesting that this drug could have carcinogenic activity. JARC. Phenoxybenzamine and phenoxybenzamine hydrochloride. *JARC Monogr. Eval. Carcinog. Risk Chem. Hum.,* 24: 185–194, 1980; Hoffman, B. B., Lefkowitz, R. J. Adrenergic receptor antagonist. Goodman and Gilman's. *The Pharmacological Basis of Therapeutics,* eighth edition New York: Pergamon Press, c1990. p. 225.

Experiments with Cynomolgus monkeys showed that after 1 to 2 weekly intracavernous injections (of papaverine) led, after a period of 12 months, to extensive fibrosis in the distal areas of the erectile organ. In humans, this reaction could have very negative long term consequences: fibrotic corpora cavernosa become incapable of erection, Abozeid, M. et al. *J. Urol.,* 138(5): 1263–1266 (1987).

In 1986, Ishii et al injected for the first time prostaglandin $E_1$ into human corpora cavernosa for the treatment of organic impotence, Ishii, N. et al. "Therapeutic trial with prostaglandin $E_1$ for organic impotence". *Jap. J. Imp.,* 1: 54–962 (1986). See also Ishii, N. et al "Intracavernous injection of prostaglandin $E_1$ for the treatment of erectile impotence". *J. Urol.,* 141(2): 323–325 (1989). Since it is a drug of natural occurrence in the body and could be expected to cause fewer side-effects than papaverine, $PGE_1$ became rapidly and universally accepted, Jünemann, K. P. and Alken, P. *Int. J. Imp. Res.,* 1: 71–93 (1988).

The use of a triple combination of $PGE_1$, papaverine and phentolamine was introduced in 1991, Bennett et al. *J. Urol.,* 146(6): 1564–1565 (1991). However, prolonged erections have been reported following the use of such a combination, von-Heyden et al. *J. Urol.,* 149(5 Pt 2): 1288–1290 (1993).

The use of prostaglandin $E_1$ is often rejected by patients because of the painfulness of its injection. Waldhauser, M. et al., *J. Urol.,* 140(3): 525–527 (1988).

In spite of initially promising evidences of a possible role of nitric oxide (NO) in the mechanics of normal human penile erection, Rajfer, J. et al., N. Eng. J. Med., 326: 90–94 (1992) in 1992 Porst, (Porst, H., Int. J. Impotence Res., 4(Suppl. 2): A91 (1992)) compared the erectogenic efficiency of 1 mg of SIN-1 (Linsindomin-Corvasal®) against 20 μg of PGE1 (Prostavasin®), both of them administered by intracavernous vias to 40 consecutive patient complaining of erectile failure. According to the latter author: ". . . SIN-1 is considerably less effective than PGE1 and will therefore, not play a major role in the management of male impotence".

Virag, in 1982, was the first to demonstrate the erectogenic effect of a vasoactive drug injected directly into the patient's epigastric artery. The type of therapy in which the patients conduct their own treatment via intracavernous administration of drugs is called self-injection therapy. Virag. R. et al. *Angiology,* 35: 79–87 (1984). See also U.S. Pat. Nos. 4, 127,118; 4,766,889 and 4,857,059, incorporated by herein reference, in their entirety.

Alternative agents, like acetylcholine (which causes marked systemic effects but only short-lasting erections), as well as a number of orally acting vasoactive substances such as yohimbine, Terbutalin, betanechol, levodopa, Verapamil or theophylline have not been successful for the treatment of male erectile dysfunction.

There is a clear need for the development of new drugs capable of acting by injection or topical administration, as facilitators, potentiators and inducers of full penile erection in man, and have reduced or diminished side effects over the current methods of therapy for the diagnostic and therapeutic treatment of various erectile dysfunction's in men.

DETAILED DESCRIPTION OF THE INVENTION

The present invention provides for the use of a histamine $H_2$ receptor agonist and/or a histamine $H_3$ receptor agonist, or pharmaceutically acceptable salts thereof, alone or in combination with other agents, for the treatment of erectile dysfunction's in animals, and human beings.

Histamine and some of its $H_2$ and $H_3$ agonists relax smooth muscle of the penile tissue and thus exhibit desired diagnostic and therapeutic activity. Adaikan et al. showed that corpus cavernosum muscle of the human penis contains both $H_1$ and $H_2$ histamine receptors. In vitro, histamine can cause three types of effects on such muscle; a contraction in 62.5% of the cases; relaxation in 28.3% and a biphasic response of contraction followed by relaxation, in 9.4% of them. The contractile response of histamine is antagonized by mepyramine, an $H_1$ receptor antagonist, but not by prostaglandin antagonists, nor by phentolamine, an α-adrenoreceptor blocker. The relaxant effect of histamine was selectively blocked by burimamide, a selective $H_2$-receptor antagonist, but not by propanolol, a β-adrenoreceptor blocker, Adaikan et al, *Euro. J. of Pharm.,* 45, pp 261–265 (1977).

In 1988, Nahoum et al, Proceedings of the Third Biennial World Meeting on Impotence, Boston, p. 43, performed for the first time, the intracavernous injection of histamine in human beings. In an intriguing fashion, in spite of the findings of Adaikan et al. in vitro, it was found that following intracavernous administration, in the human, histamine almost invariably induces corpus cavernosum smooth muscle to relax, an effect expressed by tumescence and partial or full erection of the organ. The absence of a response or, alternatively, a discrete, very transient contraction of the organ, were only rarely observed. Human testing, by intracavernous administration, showed that histamine, with or without concurrent injection of phentolamine, caused marked penile erection of both, the cavernous and the spongious bodies. Papaverine in contrast, led only to cavernous body erection, therefore causing the glans penis to remain in the flaccid state.

Aiming tat the neutralization of the patient's anxiety, exhibited as a consequence of the anticipation of a penile needle puncture, histamine was tried in combination with sulpiride, a dopaminergic $D_2$-receptor antagonist possessing tranquilizing actions. By itself, sulpiride also produces penile tumescence and even erection, supporting the hypothesis of the presence of $D_2$-receptors in human cavernous smooth muscle fibers and/or their adrenergic nerve terminals. The combination of histamine and sulpiride, enhanced the degree and duration of penile rigidity.

Further work in this aura, led to the hypothesis that histamine may be a physiological, non-adrenergic, non-cholinergic transmitter of human penile erection. Adaikan, P. G., in World Book of Impotence, Ed. by Tom F. Lue, Smith-Gordon and Nishimura Co., 52–54, (1992).

The use of histamine itself is not ideal, although it is surprisingly free of undesirable collateral effects at either the local or systemic level, following Intracavernous injection of doses of histamine capable of inducing erection, Nahoum et al, Int. J. Impotence Res., 2, Suppl. 2, 321–322 (1990). Histamine releases adrenaline from suprarrenal glands by an $H_1$-receptor-mediated mechanism. Staskewska-Barczak, J. et al., Br. J. Pharmacol., 25 (30): 728–742 (1965); West, G. B. Prog. Drug Res., 28: 9–52 (1984). For this reason, histamine injection may be dangerous in hypertensive individuals, especially when afflicted by pheochromocytoma. Furthermore, by acting on $H_1$ receptors in the respiratory tree, histamine may cause bronchospasm in asthmatic patients, Laitienen et al, Am. Rev. respirat. Diseases, 114, 291–295 (1976), Brown et al, J. Appl. Physiol. 42, 221–227 (1977).

It should be realized that from the viewpoint of its (histamine's) use as an erectogenic agent, following intracavernous injection, histamine binds, in aleatory fashion, both to $H_1$ (contractile) and $H_2$ (relaxing) receptors. Therefore, in theory, its desirable relaxing action will be partly or fully set off by its simultaneous contractile effects.

The existence of $H_1$ receptors in human skin, limits the concentration of histamine which may be used in a topical preparation. The dose of histamine which must be used to cause expressive erection will also cause the organ to show signs of local irritation. However, the use of topical preparations of histamine in combination with another agent which could reduce the amount of histamine needed would be of interest and is further described herein.

Consequently, the present invention has found that $H_2$ receptor agonists demonstrates the same erectogenic actions of histamine due to its $H_2$ receptor activation without the negative side effects of histamine and $H_1$ receptor activity.

Another aspect of the present invention is the use of a pharmaceutical composition of an $H_2$ receptor agonist and a pharmaceutically acceptable carrier or diluent in the treatment of male and female sexual dysfunction or impotence. A preferred pharmaceutical composition for use herein comprises the $H_2$ agonist, N-[2-(5-Methyl-4-imidazolyl)methylthio)ethyl]-N'-[3-(4-imidazolyl)propyl]-guanidine) and pharmaceutically acceptable salts thereof (herein referred to as Impromidine). Preferred salt forms for use in the composition are the trihydrochloride, dihydrochloride and dioxalate salts.

A further aspect of this invention is the use of $H_2$ receptor agonists in combination with at least one other therapeutically active agent. Such agents include other known facilitating, potentiating agents and/or erectogenic agents, such as but not limited to those described below. A preferred $H_2$ agonist for combination use herein is Impromidine and pharmaceutically acceptable salts thereof. A preferred combination comprises and $H_2$ agonist, such as Impromidine and at least one therapeutic agent selected from sulpiride, papaverine, phentolamine, $PGE_1$, histamine, phenoxybenzamine, an $H_3$ agonist or an $H_1$ antagonist.

Initial studies with the selective $H_2$-receptor agonists, such as Impromidine and Dimaprit, which are practically devoid of activity on $H_1$ receptors, have shown that they do not involve the drawbacks and limitations of the prior art agents, especially if the are associated with effective carriers for delivery.

Penile erection comprises three basic physiological mechanisms: a) relaxation of the trabecular smooth muscle of corpora cavernosa; b) penile cavernous and helicine arteries dilation; c) blockade of penile venous blood cutflow.

When injected by Intracavernous via histamine clearly induces both erectile smooth muscle relaxation and penile arteries dilation. These effects can be easily demonstrated by duplex scan examination of the organ under this procedure. Aiming to verify if histamine as well as it's $H_1$ agonist (2-(2-Aminoethyl)thiazole) and it's $H_2$ agonist Dimaprit could exert some contractile affect on human penile veins, another group of in vitro experiments was done utilizing surgical samples of deep dorsal being of human penis. Neither histamine nor its referred $H_1$ and $H_2$ agonists exhibited any contracting activity on the material analyzed. Nahoum et al., Itl. J. Impotence Res., 2 (Suppl.2): 321–322 (1990).

Suitable $H_2$ agonists for use herein are described in U.S. Pat. No. 4,013,659, and U.S. Pat. No. 4,126,670 whose disclosures are incorporated herein by reference in their entirety.

The compounds of U.S. Pat. No. 4,013,659 are represented by the formula:

$$\text{HET—CH}_2\text{SCH}_2\text{CH}_2\text{NH—C(=NH)—NH(CH}_2)_3\text{—HET'} \quad \text{(I)}$$

wherein

Het is a 4-imiazolyl, 5-methyl-4-imidazolyl, 5-ethyl-4-imidazolyl, 5-halogeno-4-imidazolyl, 2-thiazolyl, 3-isothiazolyl, 4-halogeno-3-isothiazolyl, 2-pyridyl, 3-methyl-2-pyridyl, 3-ethyl-2-pyridyl, 3-halogeno-2-pyridyl, 3-hydroxy-2-pyridyl, 3-methoxy-2-pyridyl or 3-ethoxy-2-pyridyl ring;

Het' is a 4-imidazole ring;

halogeno is bromo or chloro; or a hydrate or pharmaceutically acceptable salt or hydrated salt thereof Preferably Het is a thiazolyl or 5-methyl-4-imidazolyl. More preferably Het is 5-methyl-4-imidazolyl. Preferably the acid addition salts include those with hydrochloric, hydrobromic, hydriodic, sulphuric, maleic and oxalate. Preferred salts are the hydrochloric and oxalate.

Specifically exemplified compounds of Formula (I) include
N-[3-(4-Imidazolyl)propyl]-N'-[2-(4-methyl-5-imidazolylmethyl-thio)ethyl]guanidine; (also named herein as N-[2-(5-Methyl-4-imidazolyl)methyl-thio) ethyl]-N'-[3-4-imidazolyl)propyl]-guanidine);
N-[3-(4-Imidazolyl)propyl]-N'-[2-thiazolylmethylthio) ethyl]guanidine;
N-[3-(4-Imidazolyl)propyl]-N'-[2-(4-imidazolylmehylthio) ethyl]guanidine;
N-[3-(4-Imidazolyl)propyl]-N'-[2-((5-bromo-4-imidazolyl) methylthio)ethyl]guanidine;
N-[3-(4-Imidazolyl)propyl]-N'-[2-(3-isothiazolylmethylthio)ethyl]guanidine;
N-[3-(4-Imidazolyl)propyl]-N'-[2-(4-bromo-3-isothiazolyl) methylthio)ethyl]guanidine;
N-[3-(4-Imidazolyl)propyl]-N'-[2-(2-pyridylmethylthio) ethyl]guanidine,
N-[3-(4-Imidazolyl)propyl]-N'-[2-((3-methyl-2-pyridyl) methylthio)ethyl]guanidine;
N-[3-(4-Imidazolyl)propyl]-N'-[2-((3-bromo-2-pyridyl) methylthio)ethyl]guanidine;
N-[3-(4-Imidazolyl)propyl]-N'-[2-((3-chloro-2-pyridyl) methylthio)ethyl]guanidine;
N-[3-(4-Imidazolyl)propyl]-N'-[2-((3-hydroxy-2-pyridyl) methylthio)ethyl]guanidine;
N-[3-(4-Imidazolyl)propyl]-N'-[2-((3-methoxy-2-pyridyl) methylthioethyl]guanidine;
N-[3-(4-Imidazolyl)propyl]-N'-[2-((3-ethoxy-2-pyridyl) methylthio)ethyl]guanidine;
N-[3-(4-Imidazolyl)propyl]-N'-[2-((3-ethyl-2-pyridyl) methylthio)ethyl]guanidine; and
N-[3-(4-Imidazolyl)propyl]-N'-[2-(4-imidazolylmethylthio) ethyl]guanidine.

A preferred compound is N-[3-(4-Imidazolyl)propyl]-N'-[2-(4-methyl-5-imidazolylmethyl-thio)ethyl]guanidine and salts thereof, preferably the di-and tri-hydrochloride salts or the dioxalate salt, most preferably the tri-hydrochloride salt.

Compounds of U.S. Pat. No. 4,126,670 are represented by the formula:

(II)

wherein $R_1$ and $R_2$ may be the same or different and are methyl or ethyl, or the pharmaceutically acceptable salts thereof.

Exemplified compounds of Formula (II) are:
S-[3-Dimethyl-aminopropyl]isothiourea;
S-[3-Dimethyl-aminopropyl]isothiourea dihydrochloride
S-[3-Dimethyl-aminopropyl]isothiourea dihydrochloride;
S-[3-(Ethylmethylamino)prop]isothiourea dihydrochloride; and
S-[3-(Ethylmethylamino)propyl]isothiourea dihydrochloride.

A preferred compound of formula (II) is (3-diethyl-aminopropyl)isothiourea and pharmaceutically acceptable salts thereof, such as the di-hydrochloride salt also referred to herein as Dimaprit.

Suitable $H_3$ agonists for use herein are those compounds disclosed in U.S. Pat. Nos. 4,767,778; 5,047,418; EP 338, 939 A1; WO 91/17146; EP 0 458,661 and EP 0 531 219 A1 whose disclosures are incorporated by reference herein in their entirety.

Compounds of U.S. Pat. No. 4,767,778 are represented by the formula:

(III)

wherein $R_1$, $R_2$, $R_3$ and $R_4$ are each hydrogen or methyl, or $R_1$ and $R_2$ taken together represent a methylene, and $R_3$ is hydrogen, a methyl or a carboxy with the proviso that $R_1$, $R_2$, $R_3$ and $R_4$ are not simultaneously methyl groups, or a pharmaceutically acceptable salt thereof

Exemplified compounds of Formula (III) include the R and S (-)/(+) stereoisomers of:

α-methylhistamine (also called 4-(2-aminopropyl) imidazole; ($R_1$=$CH_3$ and $R_2$, $R_3$, and $R_4$=H)
β-methyl histamine (also called 4-(1-methyl-2-aminoethyl imidazole); ($R_2$=$CH_3$ and $R_1$, $R_3$, and $R_4$=H);
β,β-methyl histamine (also called 4-(1,1-dimethyl-2-aminoethyl imidazole); ($R_2$ & $R_4$=$CH_3$ and $R_1$ and $R_3$=H);
2-(4-imidazolyl)-cyclopropylamine ($R_3$ and $R_4$=H and $R_1$ and $R_2$ together form a methylene);
α-methylhistamine ($R_1$=$CH_3$, $R_3$ is COOH, $R_2$ and $R_4$ are H) ; and the pharmaceutically acceptable sets thereof
Preferred is R-α-methylhistamine and salts thereof
WO 91/17146 discloses compounds wherein the amine function of the compounds of Formula (III) is blocked to allow a bond which hydrolyzes slowly. Compounds of WO 91/17147 correspond to the formula:

(IV)

wherein $R_1$, $R_2$, $R_3$ and $R_4$ are as described in Formula (III); and is a group hydrolyzable to the free amine.

Suitably, $R_5$ is a cyclic aryl or heteroaryl group, optionally bonded to $R_6$ and is optionally mono- or poly- substituted with $R_7$; $R_6$ is H, OH, $CH_3$, O-allyl, COOH or $CO_2$alkyl, halogen, $CF_3$, alkyl, or an aliphatic or cyclic chain, aromatic or not; optionally $R_6$ may be equal to $R_5$ and $R_7$; $R_4$ is H, OH, $CH_3$, $OR_6$, $COOR_6$, halogen, $CF_3$, or optionally substituted alkyl; or pharmaceutically acceptable salts thereof.

Exemplified groups of the hydrolyzable amine are:

Preferred salts herein for compounds of Formula (IV) include the hydrochloride or maleate salt. Preferred derivatives of histamine for use with the blocked amine is (R) α-methylhistamine, α,α-dimethylhistamine and α,β-dimethylhistamine, and in particular the α-R and β-S forms.

Suitably, $R_7$ is OH, methoxy, methyl, dimethylamino, halogen or $COOCH_3$ and $R_6$ is phenyl, hydrogen or methyl. Alternatively, $R_7$ is OH, methyl, dimethylamino, or halogen, and $R_6$ is hydrogen or methyl.

An exemplified compound of formula (IV) is (R)-(−)-2-[N-(1H-imidazole4-yl)-2-propyl]-(iminophenylmethyl)] phenol, and salts thereof.

Compounds of U.S. Pat. No. 5,047,418 correspond to the formula:

wherein X is $CH_2$ or S; or a pharmaceutically acceptable salt thereof.

Exemplified compounds of Formula (V) are:
S-[2-4(5)-imidazolyl)ethyl]isothiourea (X=S); and
4-(4(5)imidazolyl)butyramide (X=$CH_2$) and salts thereof

Pharmaceutically acceptable acid addition salts for use herein include hydrochloric, hydrobromic, sulphuric, phosphoric, acetic, citric, maleic, lactic, ascorbic, fumaric, oxalic, methansulphonic and ethanesulphonic acids.

Compounds of EP 0 458 661 correspond to the formula:

also called N-methyl S-[2-(4(5)-imidazolyl)-ethyl] isothiourea and pharmaceutically acceptable salts thereof.

Compounds of EP 0 531 219 correspond to the formula:

wherein X is O or $CH_2$, and the respective N-methyl derivatives thereof as well as N-methylated S-[2-(4(5)-imidazolyl)-ethyl]isothiourea and its N-methylated version and hydrates or pharmaceutically acceptable salts thereof.

Other medicaments used to treat impotency or sexual dysfunction which may be used in combination with the $H_2$ or $H_3$ agonists include those well known to those skilled in thee art as well as those found in U.S. Pat. Nos. 5,190,967; 5,177,070; 4,663,318; 5,147,855; 4,663,318; 5,145,852; 5,104,655; 4,931,445; 4,521,421; and WO 92/21346 whose disclosures are incorporated by reference herein in their entirety.

Compounds of U.S. Pat. No. 5,190,967 correspond to the formula:

wherein
R is hydrogen, or $C_{1-6}$ alkyl, $C_{3-7}$ cycloalkyl $C_{1-6}$ alkyl, $C_{3-6}$ alkenyl, $C_{3-6}$ alkynyl, $C_{3-7}$ cycloalkyl, aryl$C_{1-5}$aryl, CHO;

$R_1$ and $R_2$ may be the same or different and represent hydrogen, halogen, $C_{1-4}$ alkyl, $C_{1-4}$ alkoxy, hydroxyl, Myano, nitro and $NR_3R_4$;

$R_3$ and $R_4$ are each independently hydrogen or alkyl;

X is oxygen or —$CH_2$—; or physiologically acceptable salts or hydrates thereof.

Exemplified compounds of formula (V) are:

Trans-5-fluoro-2,3,3a,9a-tetrahydro-1H-[1,4]-benzodioxino[2,3-c]pyrrole, and its salts, preferably the hydrochloride salt, its hydrated form, prefer the form;

Trans-5-fluoro-1,2,3,3a,9,9a-hexahydro-[1]-benzopyranyl[2,3-c]pyrrole, its salts, preferably the hydrochloride sat, and its hydrated and non-hydrated forms.

The use of galanthamine for treatment of physiologic and psychogenic mediated male erectile impotence is disclosed in U.S. Pat. No. 5,177,070 and U.S. Pat. No. 4,663,318.

Vasoactive intestinal peptide (VIP) and active fragments coupled to hydrophobic moieties thereof is disclosed in U.S. Pat. No. 5,147,855. Various long aliphatic carboxylic acid chains are attached to the N-terminus of the 28 amino acid peptide (VIP), such as $CH_3(CH_2)_{16}CO$—, in particular steryl-VIP is preferred.

U.S. Pat. No. 5,145,852 discloses a composition of papaverine, an α-blocker, a phoshopdiesterase inhibitor (PDE) and optionally $PGE_1$, a dopaminergic agent, and an atropinic agent (an anticholinergic agent). Suggested PDE agents are dipyridamol type inhibitors, and the suggested dopaminergic agent is piribedil, the $α_1$-blocker ifenprodil tartrate, yohimbine as an $α_2$ blocker, and for the prostaglandin, alpostil is suggested.

U.S. Pat. No. 5,104,655 discloses polyunsaturated fatty acids in the form of mono-, di- and tri-glycerides or in complexes with natural or synthetic phospholipids. In particular, ximenic or ximeninic acid alone, as a mono-, di- and tri-glyceride or phospholipid complex is preferred.

U.S. Pat. No. 4,931,445 discloses the use of etoperidone and pharmaceutically acceptable salts thereof, specifically the hydrochloride salt for use in treatment of male sexual impotence.

U.S. Pat. No. 4,521,421 teaches the use of sulpiride to prevent sexual stimulate responses to erectogenic agents contrary the its use herein as an adjunct with histamine and the $H_2$ and $H_3$ agonists.

PCT Patent WO 92/21346, published Dec. 10, 1992 discloses the use of 3-morphonino-sydnoimine (Linsidomin), a nitric oxide donor, for the treatment of erectile dysfunction in both animals and humans. Linsidomin is an active metabolite of molsidomine, used in coronary heart disease and also a nitric oxide donor. Endothelium derived relaxing factor, believed to be a closely related substance to nitric oxide, have been recognized as important factors in the modulation of corporeal smooth muscle tone. Ignarro, L. J. et al, Biochem. Bophys. Res. Comm., 170: 843–850 (1990); Holmquist F., et al. Acta Physiol. Scand., 141: 441–442 (1991).

Another aspect of the present invention for treatment of male and female sexual dysfunction in a animal, including human beings is the use in such treatment of an $H_3$ agonist, or a pharmaceutical composition comprising an $H_3$ agonist in a pharmaceutically acceptable carrier or diluent. The $H_3$ agonist used herein may also be administered in combination with a known, second therapeutically active compound. Therefore another aspect of the present invention is a pharmaceutical composition comprising an $H_3$ agonist and at least one additional therapeutically active agent in a pharmaceutically acceptable carrier or diluent for treatment of sexual dysfunctions in an animal. Such agents include, but are not limited to sulpiride, papaverine, phentolamine, $PGE_1$, histamine, phenoxybenzamine an $H_2$ agonist, or an $H_1$ antagonist. Preferred $H_2$ agonists for use as a co-administered agent is Impromidine or Dimaprit, more preferably Impromidine.

A "therapeutically active compound" for use herein is a substances that work as facilitators, potentiating agents and/or as erectogenic agents. Such agents include, but are not limited to, paracrine mediators such as prostaglandins and analogs thereof having vasoactive functions, such as $PGE_1$ and $PGE_2$, alprostadil and misoprostol; histamine; peptides such as calcitonin gene related peptides (CGRP) or vasoactive intestinal peptide (VIP); calcium antagonists or blockers, such as nifedipin, verapamil, diltiazem, gallopamil, niludipin, nimodipin, nicardipin, prenylamin, fendilin, terodilin, nisaldipin, nitrendipin or perhexilin; α-adrenergic receptor blockers, for example, phentolamine, phenoxybenzamine, dibenamine, doxazosin, terazosin, tolazoline, prazosin, trimazosin or minoxidil; adenosine, ergot alkaloids, chlorpromazine, haloperidol, yohimbine; or smooth muscle relaxers, such as papaverine, the nitrates, such as nitroglycerin, isosorbide dinitrate, sodium nitroprusside or s-nitroso-n-acetyl-penicillin: dopaminergic receptor antagonists, such as sulpiride or alizapride; nitric oxide releasors such as molsidomine or linsidomin; cyclooxygenase inhibitors such as indomethicin; and $H_1$ antagonists, such as astemizole, cyproheptadine, diphendhydramnine, hydroxyzine, cetirizine, mepyramine, chlorpheneramine, brompheneramine, promethiazine, and pyrilamine. Also noted for being able to produce erections are the dopamine agonists such as apomorphine and bromocriptine and opioid agonists such as naltrexone. S. Lal et. al., Pro. Neuro-Psychopharmacology, 13, pp 329–339 (1989) and Fabbri et al., Psychoneuro-endocrinology, 14, (½), 103–111 (1989).

As used herein "erectile dysfunction"or "male sexual dysfunction" refers to certain disorders of the cavernous tissue of the penis and possibly the associated fascia which produce impotence, the inability to attain a sally functional erection.

As used herein "sexual dysfunction" refers to both male and female sexual dysfunctions, and includes for women organic dysfunctions related to clitoridal disturbances.

As used herein, "animals" includes mammals, preferably human beings, but also includes the areas of animal husbandry for which such treatment may be necessary, such as but not limited to poultry farming.

METHODS OF ADMINISTRATION

The $H_2$ and $H_3$ agonists alone or in combination with additional therapeutically active agents, such as facilitators, potentiating or erectogenic agents, may conveniently be administered by any of the routes conventionally used for such drug administration, for instance, by injection, such as by intracavernous (also referred to as i.c.), intraurethral, such as by suppository or by gel, foam, lotion, ointment, cream, or sprays with direct administration into the urethra by any means available for such delivery, and by direct topical administration which include the same liniments, lotions, creams, ointments, foams, gels, pastes, drops, solutions, and sprays, as for intraurethral administration as well as a transdermal systems.

The compounds used herein may be administered in such dosage forms may prepared by combining the $H_2$ or $H_3$ agonist with standard pharmaceutical carriers according to conventional procedures. These procedures may involve mixing, granulating and compressing or dissolving the ingredients as appropriate to the desired preparation. It will be appreciated that the form and character of the pharmaceutically acceptable character or diluent is dictated by the amount of active ingredient with which it is to be combined, the route of administration and other known variables. The carrier(s) must be "acceptable" in the sense of being compatible with the other ingredients of the formulation and not deleterious to the recipient thereof.

Lotions according to the present invention include those suitable for application to the skin and for intraurethral use and may comprise a sterile aqueous solution which optionally contains bactericides, penetration enhancers, etc. and may be prepared by methods similar to those for the preparation of sterile aqueous formulations and such methods are well known to those skilled in the art. Lotions or liniments for application to the skin, or intraurethral, may also optionally include a moisturizer, such as glycerol, or oils, such as castor oil or arachis oil.

Creams, ointments or pastes, according to the present invention, are semi-solid formulations of the active ingredient for external application to the skin or for intra-urethral use. They may be made by mixing the active ingredient(s) in finely-divided or powdered form, alone or in solution, or suspension in an aqueous or non-aqueous fluid, and optionally utilize a greasy or non-greasy base. The base may comprise hydrocarbons such as hard, soft or liquid paraffin, glycerol, beeswax, a metallic soap; a mucilage; an oil of natural origin such as almond, corn, arachis, castor or olive oil; wool fat or its derivatives or a fatty acid such as steric or oleic acid together with an alcohol such as propylene glycol or a macrogel. The formulation may incorporate any suitable surface active agent such as anionic, cationic or non-ionic surfactants, such as a sorbitan ester or a polyoxyethylene derivative thereof Suspending agents such as natural gums, cellulose derivatives or inorganic materials such as silicaceous silicas, and other ingredients such as lanolin, may also be included. Also the formulations may optionally include suitable penetration enhancer.

Drops according to the present invention may comprise sterile aqueous or oily solutions or suspensions and may be prepared by dissolving the active ingredient in a suitable aqueous or saline solution which may optionally include a bactericidal and/or fungicidal agent and/or any other suitable preservatives, and optionally include a surface active agent as well as penetration enhancers, stabilizers, antioxidants, etc. The resulting solution is then sterilized in any suitable manner well known to those skilled in the art. One such manner may be to clarify the solution by filtration, transfers it to a suitable container which is then sealed and sterilized by autoclaving or maintaining at 98–100° C. for about a half an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), benalkonium chloride (0.01%) and chlorhexidine acetate (0.01%). Suitable solvents for the preparation of an oily solution include glycerol, diluted alcohol and propylene glycol.

Suitably, compounds of the present invention can be administered parenterally, that is by intramuscular or intracavenous administration. The intracavenous form of parenteral administration are generally preferred. Appropriate dosage forms for such administration may be prepared by conventional techniques requiring sterile formulations and packaging requirements. A parenteral application is preferred, since it is the safest way to directly apply a designated amount, without further adulteration by other factors.

A sterile, single use application is especially preferred for ease of application, which, in addition to optionally containing sterile, disinfected swabs and enclosed usage information, single use offer application ease and contains per dose, an effective amount of an erection producing substance of an $H_2$ or $H_3$ agonist, preferably of Impromidine. The needles used for single use prepared injections are primarily of the ultra thin variety, such as those used in insulin therapy. Also preferred are the self injection pens which are easier to handle.

The prepared injections may be kept in light impermeable containers, if necessary. For instance, the compounds of Formula (I), are light sensitive and should be kept such containers. They may also be developed in such a way so that the active ingredient and any second non-physically compatible second therapeutic agent can be mixed directly before the injection. This can take place, for example, in two containers, ampoules, or needles.

It is also possible to add photoprotective agents to the (parenteral) preparations if necessary. Several such photostabilizers are disodium edetate (EDTA), sodium metabisulphite, sodium thiosulphate, di-methionine, sodium benzoate, glycerin, methyl paraben, glutathione, urocanic acid, thiourea, and sodium urate.

The application kits for the present invention may be single use or multiple use and may also contain additional therapeutic agents for injection, topical or intraurethral application. The kits may contain single or multiple dose suppositories, for instance, which can be used for incremental increases in dosage to obtain the most effective dose for the individual and can contain one or more suppositories, or creams, or foam etc. of different therapeutic agents to enhance, or prolong, the desired effects.

Preparations for parenteral application can be packaged separately, for example in ampoules or vials. Solutions containing the active ingredient are preferably sterile water or saline solutions, but may also be prepared as an emulsion, microemulsion or suspension. The injection methods used herein can be offered fully prepared, or they can be prepared directly before use by mixing the active ingredients, for example the lyophilics, with the desired solvent or suspension ingredients, if necessary, with additional solid carrier ingredients.

As noted, the preferred solvent or carrier is water, or saline or a combination solvent with is admixable with water. Such solvents include but are not limited to various alcohols, i.e. ethanol, or isopropyl alcohol, benzyl alcohol; 2-octyl dodecane, polyethylene glycol, glycerin, propylene glycol and derivatives thereof, dioxane (diethylene dioxide), dimethyl sulfoxide, dimethyl formamide, methylcellulsolve, cellusolve, and cyclohexanone, etc., are suitable if not deleterious to the mammal.

Parenteral, as well as topical forms may be sterilized and/or, if necessary, contain auxiliary materials such as preservatives, stabilizers, wetting agent, penetration enhancers, emulsifiers, release materials, solvent conductors, salts for the control of osmotic pressure, or buffering and/or viscosity regulators.

Such additives are, for example, tartrate and citrate buffers, ethanol, complexing agents, EDTA (ethylenediamine tetraacetic acid) and its nontoxic salts. To control viscosity, high molecular polymers are suitable, for example, fluid polyethylene oxide, carboxymethylcellulose, polyvinylpryrrodilone, dextran or gelatine. Solid carrier materials are, for example, starch, lactose, mannitol methylcellulose, talcum, highly dispersed silicic acid, high molecular fatty acids (such a stearic acid), gelatine, agar-agar, calcium phosphate, magnesium stearate, animal and vegetable fats, solid, high molecular polymers (such as polyethylene glycol).

Oily suspensions for parenteral or topical uses may be synthetic vegetable oils such as liquid fatty acid esters, with $C_{8-22}$ atoms respectively in the fatty acid chains, for example, palmitic acid, lauric acid, tridecyl acid, margaric acid, stearic acid, oleic, linoleic, linolenic, arachidic acid, myristic acid, palmitic, palmitoleic, behemic, gadoleic, linoleic acid, elaidin acid, brasidin, erucic acid Lignoceric or oil acids, which are esterified with one to three type of alcohols which carry 1 to 6 carbon atoms, for example, methanol, ethanol, propanol, butanol, pentanol or its isomers, glycol or glycerol. A fatty acid composition which is available commercially is MYVEROL 18-99.

Also suitable are oils of varying viscosity such as the silicon oils or fatty alcohols, such as isotridexyl alcohol, 2-octyldodecane, cetylstearyl alcohol or oleyl alcohol, fatty acids such as oleic acids. Furthermore, oils, such as natural or hydrogenated vegetable oils, almond oil, cottonseed oil, peanut oil, or soybean oil, ethylene glycol, or fish oils containing primarily long-chain triglycerides; for example polyoxyethylene glycolate natural or hydrogenated vegetable oils, such as olive oil, sesame oil, peanut oil; hydrogenated castor oils; safflower or sunflower oils, or soybean oil may be used. The aforementioned materials have the characteristic of being spreadable, i.e. they are easily distributed on the skin.

Among the many suitable fatty acid esters useable herein are those oils containing primarily medium chain fatty acid triglycerides, such as the neutral plant oils, i.e., coconut oils, commercially available under the trade name Miglyol (BASF); Miglyol 810 and 812—fractionated coconut oil comprising capryl-capric acid triglycerides; Miglyol 818—a caprylic /capric/linoleic acid triglyceride; suitable caprylic-capric acid triglycerides such as those known under the trade name Myritol; or Captex 355—a caprylic/capric acid triglyceride; Other suitable agents are Captex 300, Captex 350, Captex 800, and Captex 850, all trade names available by Karishams Lipid Specialties, Columbus Ohio); and Mazol 1400 (trade name available through Mazer Chemical, Gurnee, Ill.); isopropylmyristate, isopropylpalmitate isopropylstearate, PEG 6-capric acid,, polyoxyethylene glycerol trioleate, ethyloleate, waxy fey acid ester such as artificial duck gland fat, coco fatty acids-isopropylester, lactic acids-ethylester, dibutylphtalate, adipic acid diisopropyl ester, polyol-fatty acid ester, among others; also useable are the propylene glycol mono-and di-fatty acid esters, such as propylene glycol dicaprylate, dilaurate, hydroxysterate, isosterate, laurate, ricinolate, etc., Especially preferred products of this class for use herein are the propylene glycol caprylic/capric acid diesters commercially known as Miglyol 840.

Combinations of gels are entirely possible for topical and intraurethral administration. In this case, ionic macromolecules are used, such as sodium carboxymethyl cellulose, polyacrylic acid, polymethyl acrylic acid and its salts, sodium amylopectin semi-glycolate, alginic acid, or propylene glycol alginate for sodium salt, gum arabic, xanthin gum, guar gum or carrageen.

Use of film former for topical administration are also possible, and as a film former, cellulose ether may be used, which dissolves in water as well as in organic solvents, and is similar to hydroxypropylcellulose, methylcellulose, ethyl cellulose and soluble starch.

Additional other ingredients may include i) lipids, such as phospholipids (which are optionally present in a liposome or a bilayer) which may be anionic, cationic or zwitterionic, in particular lecithins, such as soya bean lecithins, egg lecithin or egg phosphatide, cholesterol or long-chain fatty acids such as oleic acid;

ii) stabilizers such as hydroxypropyl cellulose, montmorillonite or colloidal silicic acid;

iii) antioxidants such as n-propyl gallate, butylated hydroxyanisole (BHA) and mixed isomers thereof, d-α-atocopherol and mixed isomers thereof ascorbic acid, and citric acid (monohydrate)

iv) anti-microbials or preservatives, such as p-hyroxybenzoic acid ester, or benzoic acid (sodium salt), methylparaben or propylparaben;

v) other anionic surfactants such as bile salts and the alkali metal salts thereof, such as sodium taurocholate.

It may be necessary to use an absorption or penetration enhancers in the various compositions used herein. The absorption or penetration enhancers most preferably used in the compositions according to the present invention are the aliphatic sulfoxides of the formula RSOR', wherein R is an alkyl, substituted alkyl, alkenyl, or hetero group containing up to 12 carbon atoms, and R' is a low molecular weight alkyl or hydroxy-substituted alkyl group. The most commonly used of these, is dimethylsulfoxide.

In the present invention, for dermal application, dimethylsulfoxide may be diluted with an appropriate diluent which may enhance acceptability of these compositions. For example, dimethylsulfoxide-glycerin solutions of 10% to 40% glycerin content may minimize skin irritation both from the dilution of the dimethyl sulfoxide and the emollient, effects of the glycerin, which tends to soothe the irritation and skin dryness which may be caused by the dimethyl sulfoxide.

A number of other penetration enhancers can be used in the compositions according to the present invention. Among these are optically active or inactive pyroglutamates of the following formula wherein R is a linear, branched, or cyclic alkyl or alkenyl group having from 10 to 14 carbon atoms. These pyroglutamic esters are contained in large amounts in human skin, and are among the natural moisturizing factors in skin.

Among other penetration enhancers that can be used in compositions according to the present invention are glycerol monolaurate, dimethylacetamide, propylene glycol, or other organic esters such as diisopropyl adipate or isopropyl myristate. Additional penetration enhancers for use in compositions according to the present invention include surfactants such as sodium laurylsulfate and polyoxyethylene-2-sorbitan monolaurate. Another effective penetration enhancer for use in the present invention is 2-ethyl-1,3-hexanediol either alone or in combination with oleic acid. Also suitable for use herein as a penetration enhancer are the bile acid salts and various modified bile acid salts.

Another group of compounds which are useful in the present invention are penetration enhancers of the formula wherein $R_1$ and $R_2$ are identical or different and each represents H, a $C_{1-25}$ alkyl $C_{24}$ alkenyl, a ($C_{1-24}$ alkyl) carbonyl or a ($C_{2-24}$ alkenyl) carbonyl provided that $R_1$ and $R_2$ are not H at the same time, or $R_1$ and $R_2$, taken together, may form a group of the following formula:

in which $R_3$ and $R_4$ are identical or different and each represents H, $C_{1-24}$ alkyl, or $C_{1-24}$ alkenyl.

A group of penetration enhancers which can also be used are the 1-substituted azacyclopenten-2-ones, described in more detail in U.S. Pat. No. 4,444,762 to Jajadhyaksha, which patent is hereby incorporated by reference. These compounds have the structural formula:

wherein

R' is H or a lower alkyl group;

m is from 3 to 7;

n is from 0–17; and

R is $CH_3$, phenyl, substituted phenyl, or with the proviso that if m is 3 and R is —CH3, then n is not from 0 to 6. These compounds can be used either alone or with $C_3$–$C_5$ diols.

Amides of the formula $(R_1)(R_2)N—C(O)—R$, wherein $R^1$ and $R^2$ are independently selected from the group consisting of alkyl radicals and cycloalkyl radicals comprising from 1 to 20 carbon atoms and R is selected from the group consisting of alkyl radicals and cycloalkyl radicals comprising from 1 to 30 carbon atoms, and the total number of carbon atoms in the compound is at least 15 are also useful in the instant invention as penetration enhancers. These compounds are described more fully in U.S. Pat. No. 4,808,414, to Peck et al., which patent is hereby incorporated by reference.

Sugar esters on combination with a sulfoxide or phosphine oxide can also be used to enhance penetration of the active ingredients. These sugar esters include hydrocarbyl and alkyl polyoxyalkylene esters of cyclic polyhydroxy saccharides wherein at least one of the hydroxyl groups on the saccharide moiety is substituted with an acyl or polyoxyalkylene group. These compounds are described in more detail in U.S. Pat. No. 3,896,238, to Smith, which patent is incorporated herein by reference.

Suitable penetration enhancers for use herein include DMSO, bile acid salts, modified bile acid salts, propylene glycol and polyethylene glycol and analogs thereof The compositions of the present invention may be formulated into highly convenient dosage forms with thickening agents, including thickened solutions or lotions, ointments (including creams and gels), and the like.

Thickened solutions or lotions and ointments may be formed by incorporating with the penetration enhancer and the active ingredients, various gelling agents or other thickeners (viscosity increasers) which permit release of the active ingredients to the skin upon application. These forms are advantageously employed to lessen the runoff from the skin that may occur with the more fluid composition forms. Importantly, they also permit more sustained contact of the penetration enhancer with the treated surfaces, thus enhancing the speed of delivery of the active ingredients subcutaneously, and providing more accurate and controllable dosing. Accidental spilling and undesired contact with the material can also be minimized with these types of formulations.

It is advantageous to use water-dispersible agents (i.e., agents dispersible in water to form a homogeneous distribution or solution), such as the polyethylene glycols, as they are readily compatible with water or other diluents to be formulated in the compositions, and they may be readily washed from the skin following absorption into the skin of the active ingredients. Alternatively, an emulsion base may be used to impart the desired thickening effect, together with the emollient effect of the lipoid phase of the emulsion base, a better spreading and wetting effect and a retardation of any skin-drying effect of the penetration enhancing compounds. When compositions are formulated with an emulsion base, the penetration enhancer is incorporated in the water phase thereof Another category of thickening base which can also impart an emollient effect is provided by lipoidal thickening agents which are soluble in the penetration enhancer.

The water-soluble thickening bases may use polyethylene glycols of different viscosity's, depending upon the desired consisted and concentration of penetration enhancer and vasodilator and constrictor to be incorporated in the compositions. Other thickening agents include water-dispersible gums, carboxyvinyl polymers, methyl cellulose, sodium carboxyl cellulose, alginates, and the like.

Lotions and ointments incorporating emulsion bases may contain the usual ingredients to provide the base, including fatty alcohols such as cetyl alcohol, emulsifiers, wetting agents and water.

Also, as noted above, the use of emulsifiers, or wetting agents may be necessary for the various formulations used herein, and include but are not limited to such agents as, sodium lauryl sulphate, fat alcohol ether sulfates, disodium-n-lauryl-β-imino dipropionate, polyoxyethylinized castor oil, or sorbitoan monooleate, sorbitan monostearate, cetyl alcohol, lecithin, glycerine monostearate, polyoxyethylene stearate, alkyl phenol polyglycol ether, cetyltrimethyl ammonium chloride, or mono-/dialkylpolyglycol ether-orthophosphorus acid-mono-ethanolamine salts.

Pourable pharmaceutical dosages may be provided and dispensed in graduated containers, or containers which contain a given volume, such as 5 cc or the like. Containers with columns of 20 cc and above provide convenient multiple dosage forms, and those containing a typical single dose, such as from about 0.5 g to about 10 grams of a combination of vasoactive agent convenient vasodilator, penetration enhancer etc., and provide a convenient dosage form. Squeeze tubes for creams and ointments and cotton stick applicators may all be used for topical application of the thickened compositions.

The compositions of the present invention can also be administered by spraying and misting such as from misting devices and aerosol bottles, which containers are charged with fluid formulations containing at least 10% by weight of a combination of penetration enhancer, vasodilator, and vasoconstrictor, along with an aqueous diluent and, optionally, thickening agents, physiological salts, and the like. These compositions can be administered as either liquids or semisolid gels or mousses, depending upon the amount of gelling agents or surfactants included in the compositions. Compositions for this purpose are sufficiently fluid to permit dispensing by spray or mist from the container, and also meet the necessary criteria for penetrability and avoidance of undue side effects.

With respect to administration of drugs directly into the penis, medicated catheters such as those described in U.S. Pat. No. 4,640,912 have been used; a nitroglycerin coated erection inducing condom is disclosed in U.S. Pat. No. 4,829,991; transurethral administration of certain drugs is suggested in U.S. Pat. Nos. 4,478,822; 4,610,868; 4,640,912 and 4,746,508; medicated urethral suppositories, inserts or plugs typically containing anti infective agents or spermicides is disclosed in U.S. Pat. Nos. 1,187,423; 2,584,166; 2,696,209 and 3,373,746; $PGE_2$ as a selfadministered gel, cream or suppository for intraurethral delivery is disclosed in Derwent abstract 93-045213/05. Use of such delivery systems as defined above for compositions of the instant invention is contemplated and the disclosures of said references are incorporated by reference herein. PCT/ US91/ 02758 published as WO 91/16021, whose disclosure is incorporated by reference in its entirety herein, provides yet another route for intraurethral delivery for drugs used to treat erectile dysfunction.

Standard suppository bases such as glycerin, the semisynthetic glycerides, the hydrogenated triglycerides, commercially available as IV Novata, Massa Estarinum Massupol and suppocire are disclosed in the Handbook of Pharmaceutical Excipents, American Pharmaceutical Association, (1983) pp314–320 whose disclosure is incorporated by reference herein. The method of making such intraurethral suppositories (also called bougies) is well known to those skilled in the art. Suggested suppos® brands.

Alternatively, the therapeutic agents may be applied to the penis in a layered manner. This technique would require in one instance that the user first place an ointment or cream, etc. having only the carrier, and perhaps a penetration enhancer, to the area and allow it to remain there for a few minutes. It would be wiped off and a second cream or ointment, etc., applied containing the primary agent would be applied. The initial presence of the carrier provides a physiological pathway of absorption for the agent to follow. Alternatively the first layer may contain both the carrier and active agent, and optionally a penetration enhancer and the second layer may contain a second therapeutic agent, for example histamine or phentolamine. Such applications may be desirable if the two therapeutic agents and/or penetration enhancer are physically incompatible in sane base.

Alternatively, a catheter or other such suitable device ma be placed within the urethra and followed by introduction of the ointment, cream or suppository, etc. therein. Suitably the catheter may have a means of attachment for a tube to be attached, preferably single dose administration, and extrusion of the tube contents into the urethra through said catheter would take place.

It is preferred that the agents be rapidly delivered through the urethra in order to bring about a rapid onset of the desired effect. The carrier should be a rapid releasing one to allow for quick and consistent absorption of the active agent. The composition containing the active agents should contact the urethra along a surface area as large as possible, such as a 2–5 cm length, rather than a localized site along the urethra. Further, the composition should be applied at least 1 cm into the penis and past the point where the transition from the epidermal character of the gland has been completed.

It is firer desired, in all dosage forms used herein which are inserted intraurethral that the volume of composition deposited in the urethra remain there until complete absorption of the active agent(s) have occurred. Volumes in the range of 50 to 100 mg (approx 50–100 $\mu$l) tend to exhibit spillage prior to complete absorption. Accordingly, the amount of active drug containing compositions to be retained in the urethra is preferred to be about or below 100 $\mu$l and more preferably about 50 $\mu$l.

Adequate lubrication has been obtained with as little as 5–10 $\mu$l of a lubricating carrier, such as polyethylene glycol (PEG) 1000 and 1450. For intra-urethral administration, as noted above, the composition can be in the form of a fluid or semi-fluid solution, suspension, dispersion, ointment, paste, cream, or gel which may also include many other excipients, including penetration enhancers, and buffering agents, as well as antimicrobial agents or preservatives for instance. All of these can be easily introduced into the urethra from a flexible tube, squeeze bottle, pump or aerosol spray in single or multiple dose administrations. The composition may also be contained in a rapidly releasing suppository which melts and is absorbed at room temperature. See for example, Remingtons, 18th Edition. WO 91/16021 provides for devices to insert a suppository as well as coating the exterior of the urethral suppository, also disclosed are devices for delivery of ointments, pastes, etc into the urethra. Such devices and coatings would also be applicable to the instant invention herein.

The present invention may also be applied topically via a transdermal delivery system. One such delivery system is disclosed in U.S. Pat. No. 5,152,997 whose disclosure is incorporated by reference herein in its entirety.

For use herein the parenteral (i.c.) dosage of an $H_2$ agonist such as those disclosed in Formulas (I) and (II) herein, will be from about 5 mcg to 1,200 mcg per dose, preferably from about 15 mcg to about 900 mcg per administration, and more preferably from about 25 mcg to 600 mcg. For use herein the parenteral (i.c.) dosage of an $H_3$ agonist without a second agent, will be about 1,500 to about 15,000 mcg per dose, preferably from about 3,000 to about 12,000 mcg, and more preferably from about 4,500 mcg to 9,000 mcg.

If a second active agent, such as phentolamine or sulpiride is co-administered i.c. a reduction in the dosage of the $H_2$ or $H_3$ agonist is possible. It will also be appreciated by one of skill in the art that the optimal reduction in dose can be determined by conventional techniques by those skilled in art. A suitable reduction in dose of the $H_2$ agonist administered is expected and the dose, dependent upon the second agent co-administered, such as phentolamine, sulphide, or papaverine will reduce the dose to about 2.5 mcg to 150 mcg per administration, preferably about 10 mcg to 120 mcg per administration.

It will be recognized by one of skill in the art that the optimal quantity the individual dosages of the compounds used herein will be determined by the nature and extent of the condition being treated, the form, route and site of administration, and the particular patient being treated, and that such optimums can be determined by conventional techniques by those skilled in at. The dosage to be administered is obviously dependent upon species, body weight, age, individual condition and method of application. It will also be appreciated by one of skill in the art that the optimal course of treatment, i.e., the number of doses given per treatment, the frequency of such treatment and the eventual duration of use can be ascertained by those killed in the aft using conventional course of treatment determination tests.

Erection producing intracavernous doses of papaverine are typically in the range of about 7.5 to 160 mg, for e.g. phentolamine in the range of about 0.1 to 10 mg, and for $PGE_1$ in the range of 2.5 to 50 micrograms. Kurkle, et al, *Urol Cn. of America*, Vol. 15, No. 4, pp 625–629 (1988) and Ishii et al., *J. Urol.*, Vol. 141, pp 323–325 (1989). Vasoactive intestinal peptides at doses of 10 to 100 μg have been used for producing erection upon intracavernous injection.

Topical and intraurethral administration of active agents typically require higher doses and as above for the prostaglandins, such as $PGE_1$, papaverine, and the α-adrenergic agents, phentolamine, and phenoxybenzamine are well known to those skilled in the art. Generally, the unit dosage application for $PGE_1$ is in the range of from about 50 to 500 μg, preferably from about 25 to 250 μg. For papaverine, the range of from about 1,000 to 25,000 mcg, for phentolamine, prazosin and doxazosin they range from about 200 to 100 μg per dose with from about 50 to 2,000 μg being preferred. For VIP the range is from 3 mng to 10 mcg; for the dopaminergic antagonists, alizapride and alizapride from about 50 to 150 mg. In combinations of two or more drugs, such as $PGE_1$ and the α-lockers tend to potentiate the erectile effect, thereby permitting efficacy to be obtained at a lower dose of both drugs.

In a combination administration it may be advisable to administer the two agents sequentially rather than in one dosage form. Therefore another aspect of the instant invention is the sequential administration of an $H_2$ or $H_3$ agonist and a second therapeutic agent for the treatment of male or finale sexual dysfunction.

Use of intraurethral or topical administration of the instant invention would allow for the lowest effective dosage of the histamine agonists particularly when used in combination with a second agent by allowing the patient to initially titrate himself to the dosage most effective for him by using the lowest dosage and repeating administration until the desired effect is obtained. Thereafter the patient would select an effective incremental dosage that is close the determined higher dosage or could continue with multiple lower doses or multiple co-administered agents. As noted in WO 91/16021 where small intraurethral suppositories are utilized, individual titration of $PGE_1$ and prazosin were administered in multiple inserts. Similarly the $H_2$ agonist alone or in combination with a second agent or optimally the second agent would be in a second suppository to allow for incremental dosing as needed.

The amount of active ingredient required for therapeutic effect on topical or intraurethral administration will, of course, vary with the compound chosen, the nature and severity of the condition of the animal or mammal undergoing treatment, and is ultimately at the discretion of the physician or veterinarian. It will also be appreciated by one of skill in the art that the optimal reduction in dose can be determined by conventional techniques by those fled in art.

A suitable dose of an active ingredient for the $H_2$ agonists and in particular of Formulas (1) or (ED is from about 50 mcg to 2,000 mcg for topical administration, preferably from about 150 mcg to 1,500 mcg per administration, more preferably about 250 mcg to 1,000 mcg per administration. If utilized in multiple intraurethral suppositories, each suppository is preferably about 150 to 250 mcg each.

If a second active agent, such as phentolamine or sulpiride is co-administered topically or intraurethral, a reduction in the dosage of the $H_2$ or $H_3$ agonist is possible. It will also be appreciated by one of skill in the art that the optimal reduction in dose can be determined by conventional techniques by those skilled in art. However, a suitable reduction in dose of the $H_2$ agonist administered is expected and the dose, dependent upon the second agent administered, such as phentolamine, sulpiride, or papaverine will be about 30 mcg to 1,500 mcg per administration, preferably about 100 mcg to 1,000 mcg per administration.

The term "co-administration" as used herein means both the sequential administration of one agent after another and the concomitant used together, i.e. contemporaneously.

Another aspect of the instant invention is the co-administration of an $H_2$ agonist, such as Impromidine with histamine. Such co-administration of an $H_2$ agonist will allow the dosage of histamine to be significantly reduced. The dosage of histamine used will be below that which causes significant skin irritation, skin flushing and headaches, which have resulted from the higher dosages of histamine.

The dosage of histamine when administered i.c. alone is about 30 to about 120 mcg per administration. The co-administration of histamine with Impromidine will reduce the amount of histamine necessary. Preferably about a 20% reduction in amount, to about 20 mcg to 100 mcg more preferably about 45 mcg to about 90 mcg. The co-administration of histamine with Impromidine intraurethral should result in similar reduction in dosage of Impromidine at about a 20% reduction in dose, from about 50 mcg to about 1,500 mcg per administration.

If a third agent, such as phentolamine, papaverine, $PGE_1$ or sulpiride is also administered the resulting dosage of histamine and Impromidine the reduction in doses of the $H_2/H_3$ and histamine agents is ultimately at the discretion of the physician. The use of multiple intraurethral suppositories would allow for improved incremental dosing of both the $H_2$ or $H_3$ agonist with histamine and optionally a third agent such as sulpiride, papaverine, phentolamine, prazosin, or $PGE_1$.

FORMULATION EXAMPLES

Example 1

Injection solution

Solutions of 50 mcg/ml of Impromidine trihydrochloride is dissolved in an isotonic solution and buffered to physiologic pH of 5.5 to 6 with sodium hydroxide. The solution is packaged in 0.5 ml or 1ml ampoules or any suitable size ampoules as may be necessary, including multiple dose vials.

Similar solutions may be made using saline and/or sterile water optionally buffered with different agents Alternatively the amount of Impromidine trihydrochloride may be varied to further concentrate or dilute the volume. In a manner to these examples a different salt form, for instance the di-hydrochloride or di-oxalate salts may be utilized.

Alternatively the isopropyl myristate my be substituted by squalene oil, vitamin e and any low molecular weight, short chain alcohol including n-dodecanol may be used.

Example 2

Solution for topical application

A solution for topical application is prepared having 200 mcg Impromidine dihydrochloride, 2 ml isopropyl myristate and 10 ml ethanol and packaged in 2 ml dosages.

Altenivey solutions for topical application may vary the amount of Impromidine dihydrochloride to firther concentrate or dilute the volume from 200 mcg to 10,000 mcg Impromidine. In a similar manner to these examples a differen salt form, for instance the tri-hydrocworide or di-oxalate salts may be utilized.

Alternatively the isopropyl myristate my be substituted by squalene oil, vitamin e and the any low molecular weight, short chain alcholol including n-dodecanol may be used.

Example 3

Transdermal Patches 10 g linoleic acid and 90 g propylene glycol are mixed together. To this mixture, 200 mcg Impromidine tri-hydrochloride is dissolved. Gauze squares, covered on one side with artificial material, are then soaked in this solution and sealed in aluminum foil.

Alternatively the linoleic may be substituted by oleic acid.

Alternatively the transdermal application may vary the amount of Impromidine trihydrochloride to further concentrate or Impromidine volume from 200 mcg to 10,000 mcg Impromidine. In a similar manner to these examples a different salt form, for instance the di-hydrochloride or di-oxalate salts may be utilized.

Example 4

Spreadable gel 94 g purified water is warned to 70 degree Co and displaced with 500 mcg Impromidine hydrochloride. After adding 0.2 g p-hydroxybenzoic acid ester, 5 g methylhydroxyethyl cellulose is dispersed in the remaining solution. It is cooled by stirring. After cooling, a highly viscous gel is produced.

Alternatively one may vary the amount of Impromidine tri-hydrochloride to the further concentrate or dilute the volume from 200 mcg to 10,000 mcg Impromidine. In a similar manner to these examples a different salt form, for instance the di-hydrochloride or di-oxalate salts may be utilized.

Example 5

Ointment 200 mcg Impromidine tri-hydrochloride is dissolved in a mixture of 5 g benzyl alcohol, 6 g isopropyl stearate, or in a similar amount of isopropylmyristate/isopropyl palmitate/isopropylstearate mixture, 10 g vinylpyrrolidone/vinylacetate-copolymer and 89 g isopropanol. The solution may be packaged separately for liquid application, or packaged as a spray with the usual propellants.

Alternatively one may vary the amount of Impromidine tri-hydrochloride to further concentrate or dilute the volume from 200 mcg to 10,000 mcg pyridine. In a similar manner to these examples a different salt form, for instance the di-hydrochloride or di-oxalate salts may be utilized. If desired a differen $H_2$ agonist such as Dimaprit may be utilized, or alternatively a second therapeutic agent may be included. Such agents include histamine, R-α-methyl histamine or an $H_1$ antagonist.

Example 6

Oil-in Water Emulsion

In the usual fashion, a mixture is produced consisting of 200 mcg Impromidine hydrochloride, 9 g of a mixture of mono and di glycerides of palmitate and stearic acid, 3 g cetylstearyl alcohol with approx. 12 mol ethylene oxide, 10 g 2-octyldodecane, 5 g thick paraffin, 1–2% benzyl alcohol, 500 mg PHB-ester and demineralized water.

As for the above 5 examples the amount of Impromidine may be varied from 200 to 10,000 mcg and alternative salt forms may be used as well.

Example 7

Light consistency cream 200 mcg Impromidine hydrochloride, 4 g mono and diglyceride of palmitate and stearic acid, 4 g cetylpalmitate, 1 g cetylstearyl alcohol with approx. 12 mol ethylene oxide, 1 g cetylstearyl alcohol with approx. 30 mol ethylene oxide, 5 g isopropylmyristate-/isopropylpalmitate-/isopropylstearate mixture, 0.5 g weakly bound polyacrylic acid of extremely high mg, 0.11 g sodium hydroxide 45 mg 3 g glycerin, and de -mineralized water to 100 g.

As in the above noted examples the amount of Impromidine may be varied from 200 to 10,000 mcg and alternative salt forms may be used as well.

Example 8

Greaseless emulsion

A mixture of 2.5 g oleic acid decylester, 2.5 g isopropylmyristate, 4 g thin paraffin, 0.9 g polyethylene stearate, 0.6 g sorbitan and glycerin fat acid ester are bonded at 70 degree C for 10 minutes and stirred. The melted mixture is put in a 75 degree Co warm solution of 50 g demineralized water, 300 mcg Impromidine tri-hydrochloride and 100 mg allantoin and stirred, then cooled to 45 degree C. At this temperature, a carbopol film made up of 10 g ethanol, 0.7 g carbopol 934 (weaky bonded polycrylic acid) and 22.95 g demineralized water develops, which is removed with turrax, swelled to 2 h and neutralized with 0.15 g soda lime. Upon reaching 40 degree C, 1 g collagen is added. Finally, the raw emulsion is homogenized, if necessary, after the addition of 0.6 g of perfume oil, at 20 to 25 degree C in a high pressure homogenizer.

As in the above noted examples the amount of Impromidine nay be varied from 200 to 10,000 mcg and alternative salt forms may be used as well.

Example 9

Gelatin solution

For a gelatinous solution, 300 mcg Impromidine hydrochloride, 150 mg gelatin, 4.7 mg phenol are topped off with 1 ml of distilled water, placed in vials and filled to 1 ml.

As in the above noted examples the amount of Impromidine may be varied from 200 to 10,000 mcg and alternative salt forms may be used as well.

Example 10

Spray

In a mixture of 3.5 ml miglyol 812 and 0.08 g benzyl alcohol, 200 mcg Impromidine hydrochloride is suspended.

This suspension is filled into a container with a valve. Then, 5 ml freon 12 is filled into the container via the valve, under pressure. By shaking, the freon-chlorinated cfc. is released into the miglyol-benzyl-alcohol mixture.

As in the above noted examples the amount of Impromidine may be varied from 200 to 10,000 mcg and alternative salt forms may be used as well.

Example 11

Oil-in Water Creams a) 250 mcg Impromidine is dissolved in a mixture of cetylstearyl alcohol 7.2 g, polyethylene glycol 1000 monoethylether 1.8 g, white petroleum, 15 g., liquid paraffin 6 g., purified water to 100 g (and any necessary preservatives). Alternatively, 250 mcg of Dimaprit may be used.

b) 250 mcg Impromidine is dissolved in a mixture of liquid paraffin 10 g., cetylstearyl alcohol 20 gm., polyethylene glycol 1000 monocetyl ether 5 g, purified water to 100 g (and any necessary preservatives). Alternatively, 300 mcg of Dimaprit or any of its pharmaceutically acceptable salts may be used instead.

c) 250 mcg Impromidine is dissolved in a mixture of cetylstearyl alcohol 8.1 g. sodium lauryl sulphate 0.9 g, white petroleum 15 g., liquid paraffin 6 g., sodium phosphate 2.5 g, citric acid monohydrate 0.5 g, purified water to 100 g (and any necessary preservatives).

Alternatively, 300 mcg of Dimaprit or its pharmaceutically acceptable salts may be used instead.

As in the above noted examples the amount of Impromidine may be varied from 200 to 10,000 mcg and alternative salt forms may be used as well.

Example 12

Ointments a) 200 mcg Impromidine is added to a mixture of Miglyol 812 Neutral oil 30 gm., caprylic/capric/stearic triglyceride 40 gm., white petroleum 10 gm., and liquid paraffin 20 gm.

b) 200 mcg Impromidine is added to a mixture of glyceryl cocoate and hydrogenated coconut oil and ceteareth 25, 43 gm., caprylic/capric/stearic triglyceride 29 gm., Miglyol 812 Neutral oil 18 gm., and liquid paraffin 10 gm.

As in the above noted examples the amount of Impromidine may be varied from 200 to 10,000 mcg and alternative salt forms may be used as well.

Example 13

Intra-urethral suppositories

Suitable suppository bases for inclusion with the active ingredients (which may vary but suitably include Impromidine from about 15 mcg to about 250 mcg per suppository and alternate salt forms) include:

a) Macrogel 6000 (50 gm.), Macrogel 1540 (30 gm) water and medicament (20 gm);

b) Macrogel 6000 (47 gm.), Macrogel 4000 (33 gm.) water and medicament (20 gm);

c) Macrogel 1000 (75 gm.), Macrogel 4000 (25 gm.), adjust for weight of medicament;

d) Witepsol S Suppository Base plus medicament;

e) Witepsol H Suppository Base, Imwitor 742 2–3 gm, or up to 8 g. plus medicament;

f) Witepsol W Suppository Base, Imwitor 742,2–3 gm, or up to 8 g plus medicament.

In all of the above noted examples a second therapeutic agent may be added or alternatively the examples could be formulated using an $H_3$ agonist such as R-β-methyl histamine.

BIOLOGICAL DATA

IN VITRO EXPERIMENTS

Histamine action of $H_1$ reception

Figure 1:
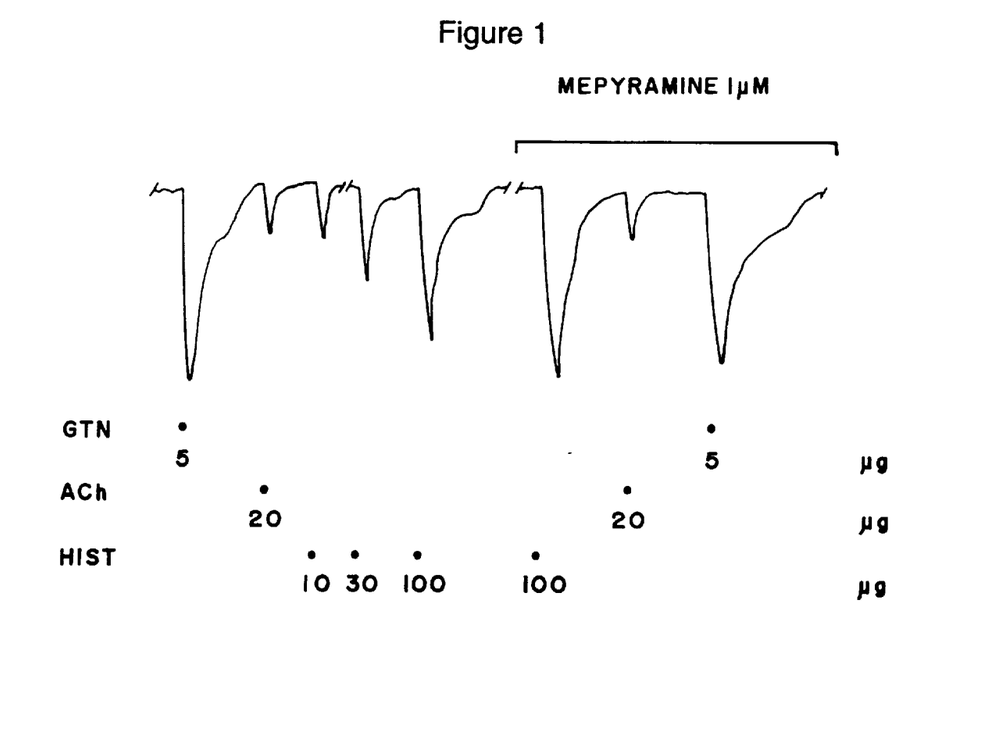

The relaxing effect induced by histamine on segments of human corpora cavernosa in vitro is demonstrated in FIG. 1. The erectile tissue of corpora cavernosa was mounted in cascade and perfused with warmed (37° C.) and oxygenated (95% $O_2$+5% $CO_2$) Krebs solution, as described in Vane, J. R Brit. J. Pharmacol., 23:360–373 (1964). Glyceryl trinitrate (GTN; 5 μg), acetylcholine (ACh; 20 μg), and histamine (HIST; 10, 30 and 100 μg) relaxed the human erectile tissue. During infusion with mepyramine (1 μM), it was observed that the relaxing responses induced by GTN and ACh were not modified, while the relaxation induced by histamine was potentiated. This figure is representative of 3 experiments.

Histamine action of $H_2$ receptors

Figure 2:
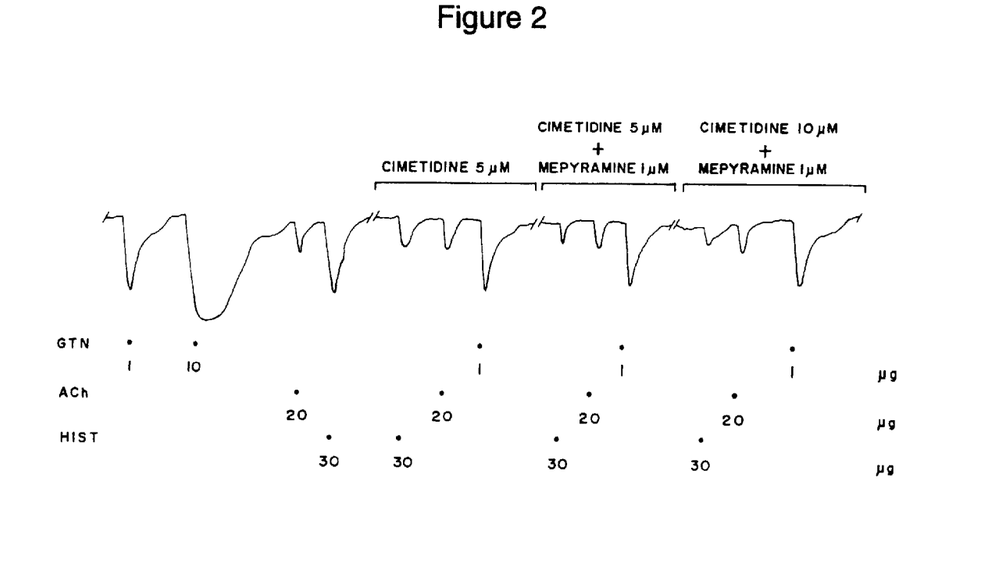

The effect of Cimetidine on relaxation caused by histamine on segments of human corpora cavernosa in shown in FIG. 2. The corpus cavernosum tissue was mounted in cascade and perfused with warmed (37° C.) and oxygenated (95% $O_2$+5% $CO_2$) Krebs solution, as described by Vane, supra. Glyceryl tinitrate (GTN; 1 and 10 μg), acetylcholine (ACh; 20 μg), and histamine (HIST; 30 μg) relaxed the human erectile tissue. During infusion with Cimetidine (5 μM), it was observed that the relaxation induced by GTN and ACh was not modified, while the relaxation induced by histamine was markedly inhibited. In the simultaneous presence of Cimetidine (5 or 10 μM) and mepyramine (1 M), histamine still produced a decreased but definite relaxing response. This Figure is representative of 3 experiments.

Histamine action of $H_3$ receptors

Figure 3:
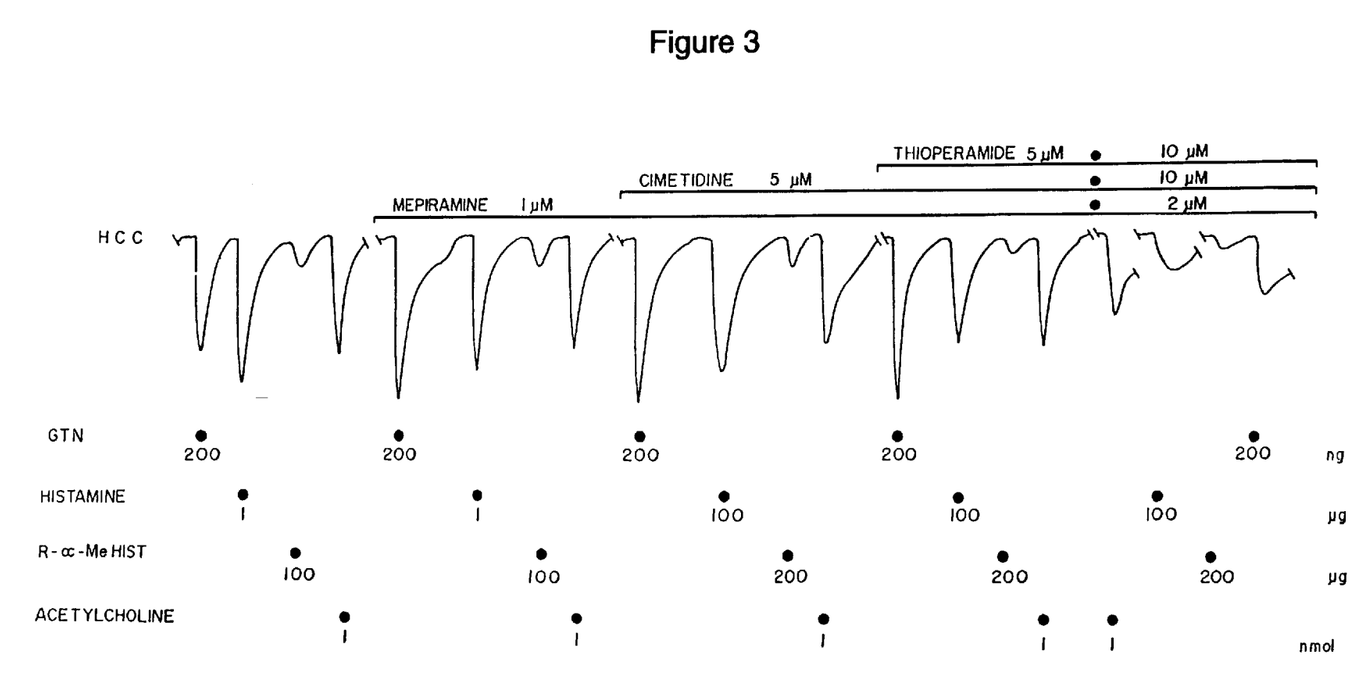

The effects of both R-a-methylhistamine (an $H_3$ agonist) and thioperamide (an $H_3$ antagonist) on strips of huan corpora cavernosa smooth muscle are shown in FIG. 3. The corpus cavernosum tissue was mounted in cascade and perfused with warmed (37° C.) and oxygenated (95% $O_2$+5% $CO_2$) Krebs solution, as described in Vane, supra. Glyceryl is trinitrate (GTN; 200 ng), acetylcholine (ACh; 1 nM), and R-α-methylhistamine (R-α-MeHIST, 200 μM) caused relaxation of human corpus cavernosum erectile tissue. The maximally effective dose of 100 μg of R-α-MeHIST had a considerably smaller relaxing effect than 1 μg of histamine. Neither mepyramine (1 μM) nor cimetidine (5 μM) altered the effect of R-α-MeHIST. Thioperamide, a specific blocker of $H_3$ histamine receptors, decreased but did not fully block the responses of human cavernous erectile tissue to R-α-MeMIST. This figure is representative of 2 experiments.

IN VIVO EXPERIMENTS

The erectogenic activity of histamine alone or in combination with phentolamine was compared to that of papaverine. These effects were studied in four patients having psychogenic and four patients having erectile disfunction of organic origin. The patients were submitted in consecutive fashion to respectively: the vehicle of the preparations (5% mannitol in phosphate buffer); papaverine (60 mg); histamine hydrochloride (30 and 60 μg); and these same doses of histamine in combination with 5 mg of phentolamine mesylate.

The control injection were innocuous; histamine alone produced erectogenic activity markedly lower than that due to papaverine, both in terms of the intensity and duration of the responses. Nevertheless, when associated with phentolamine, histamine proved to evoke erections similar to erections reported by the patients during sexual intercourse.

In none of the cases studied did histamine cause unduly prolonged erection, having a maximal course of action of 3 hours. The association of histamine with phentolamine benefited mainly the duration of histamine erection. The erectogenic resulting from the association of histamine with sulphide (100 mg) were similar to those obtained with the use of histamine associated with phentolamine (5 mg); however, sulpiride plus histamine produced a 10% greater degree of pile rigidity and a 20% longer duration of the response.

$H_1$ antagonists (mepyramine or chloroprene, 20–100 μg) potentiated the erectogenic effect of histamine in a manner similar to that caused by phentolamine. This similarity points towards the usefulness of the substitution of α-adrenergic antagonists, like phentolamine, by $H_1$ antagonist, when wing histamine or its $H_2$ or $H_3$ agonists as primary erectogenic agents.

Effects of intracavernous injections of Dimaprit in monkeys

10 μg of Dimaprit dissolved in 250 μl of distilled water were administered to 5 tufted ear (Callithrix jacchus geoffroy) either alone or in combination with 200 μg of phentolamine. This procedure invariably evoked an erectile response which was clearly intensified when the drug was administered with phentolamine.

Such results suggest the potential usefulness of Dimaprit as an erectogenic drug in the management of human erectile dysfunction, both alone or in combination with other secondary potentiating agents, such as histamine, $H_3$ agonists, $H_1$ antagonists, α-adrenergic blockers, $D_2$-receptor antagonists, NO-donors, VIP and others.

Effects of intracavernous injections of Impromidine in monkeys

Nine adult monkeys of the Callithrix genus were anesthetized with ketamine (10 mg/kg) and diazepam (0.3 mg/kg). Maximum volume injected was 0.3 ml.

Three animals were given 3.5 μg of only Impromidine. Responses were nil, partial or full in each of the animals. Six animals were given 3.5 μg of Impromidine in combination with 200 μg of phentolamine. In 3 of such animals the erectile responses varied between 60 to 80% of maximum. The remaining animals presented full erections. In all but one animal responses lasted between 10 and 40 minutes. The last animal remained in full erection for 3 hours.

Effects of intracavernous injections of Impromidine in human volunteers

Like the experimental animals, all human subjects showed some degree of erectile response when submitted to Impromidine injection by the intracavernous route. The responses were as follows: 1 patient who received 60 μg of Impromidine alone showed after 10 minutes 70% of his maximal penile rigidity. This response was maintained for 40 minutes. Of the 3 patients receiving 30 mcg of Impromidine in combination with 2.5 mg of phentolamine, 2 showed 70% of the maximal penile response and 1 patient, 40% of his also maximal response. A 70% degree of rigidity is usually sufficient for penetration; 40% is not. In 1 patient 30 μg of Impromidine was administered in association with 100 mg of sulpiride and penile tumescence was the only response observed.

Effects of intraurethral administration of Impromidine in men

The intraurethral administration of Impromidine (200 μg) together with 500 μg of phentolamine dissolved in a mixture of 5% mannitol and 5% DMSO was performed in 9 individuals: 7 normal volunteers and 2 impotent patients. 0.7 ml of the drugs' mixture were instilled into the urethra using a 1 ml plastic syringe fitted with a pippet-type tip. Following instillation, the fluid outflow was prevented by temporarily sealing of the urinary meatus with dermal adhesive tape which was kept in place until a definite erectile response was observed, or for a maximal period of 90 minutes.

Full erection was observed in 4 individuals; partial response was noted in 5; one patient exhibited only tumescence. Responses became apparent after 30 to 90 minutes according to the patient. Durations varied between 15 and 60 minutes.

It should be noted that the t was given twice to one of the patients. His responses were essentially identical Control experiments in which the drug's vehicle only was applied, gave uniformly negative results.

In an additional group of patients studied, the mixture of 500 μg of histamine plus 500 μg of phentolamine admit by the route produced comparable results.

In summary, the above considerations lead to the conclusion that: a) histamine, as well as its $H_2$ agonists, particularly Impromidine, exhibit erectogenic activity of diagnostic and therapeutic value in the management of erectile dysfunction in mammals; b) such agents activity is potentiated both regarding its intensely and duration, by concurrent or sequential administration of adequate secondary agents; c) these agents, alone or in combination, showed adequate pharmacologic activity by either intracavernous and topical, mostly transurethral or transbalance application; d) $H_3$ agonists, alone or in combination with other secondary agents, must be considered as being able to facilitate, potentiate or induce full penile erections in mammals.

The above description fully discloses the invention including preferred embodiments thereof Modifications and improvements of the embodiments specifically disclosed herein are within the scope of the following claims. Without firer elaboration, it is believed that one skilled in the art Gin, using the preceding description, utilize the present invention to its fullest extent. Therefore the Examples herein are to be construed as merely illustrative and not a limitation of the scope of the present invention in any way. The embodiments of the invention in which an exclusive property or privilege is claimed are defined as follows.

What is claimed is:

1. A method of treating male sexual disfunction in a mammal in need thereof which comprises administering to said mammal an effective amount of an $H_2$ agonist.

2. The method according to claim 1 wherein the $H_2$ agonist is a compound of the formula $$\text{Het—CH}_2\text{SCH}_2\text{CH}_2\text{NH—C(=NH)—NH(CH}_2)_3\text{—Het'} \qquad (I)$$

wherein

Het is a 4-imiazolyl, 5-methyl-4-imidazolyl, 5-ethyl-4-imidazolyl, 5-halogeno 4-imidazolyl, 2-thiazolyl, 3-isothiazolyl, 4-halogeno-3-isothiazolyl, 2-pyridyl, 3-methyl-2-pyridyl, 3-ethyl-2-pyridyl, 3-halogeno-2-pyridyl, 3-hydroxy-2-pyridyl, 3-methoxy-2-pyridyl or 3-ethoxy-2-pyridyl ring;

Het' is a 4-imidazole ring;

halogeno is bromo or chloro; or a hydrate or pharmaceutically acceptable salt or hydrated salt thereof.

3. The method according to claim 2 which is N-[3-(4-Imidazolyl)propyl]-N'-[2-(4-methyl-5-imidazolylmethylthio)ethyl]guanidine or a hydrate of pharmaceutically acceptable salt thereof.

4. The method according to claim 1 wherein the $H_2$ agonist is of the formula:

wherein $R_1$ and $R_2$ may be the same or different and are methyl or ethyl, or the pharmaceutically acceptable salts thereof.

5. The method according to claim 4 wherein the compound is (3-dimethyl-aminopropyl)isothiourea and pharmaceutically acceptable salts thereof.

6. The method according to claims 1 to 5 wherein the $H_2$ agonist is further administered in combination with one or more therapeutically active agents which are an $H_3$ agonist, histamine, an α-adrenergic blocker, a dopamine $D_2$-antagonist, nitric oxide releaser, prostaglandin or an analog thereof having a vasoactive function, calcium antagonist, CGRP, VIP, phentolamine, physiostigmine, neostigmine, hydralazine, sodium nitroprusside, phenoxybenzamine or an $H_1$ antagonist.

7. The method according to claim 6 wherein the second therapeutic agent is administered sequentially or contemporaneously with the $H_2$ agonist.

8. The method according to claims 7 wherein the second therapeutic agent is phentolamine, phenoxybenzamine, histamine, $H_3$ agonist, $H_1$ antagonist, $PGE_1$ or sulpiride.

9. The method to claim 7 wherein the $H_2$ agonist is Impromidine or Dimaprit.

10. The method according to claims 1 whereby the method of treatment is by intracavernous injection.

11. The method according to claim 1 which further comprises a second therapeutic agent which either facilitates, potentiates or is erectogenic.

12. Unit dose packaging of a single use intracavernosum injection wherein said unit dose packaging contains an effective amount of an intracavernosal formulation of an $H_2$ agonist that promotes erection.

13. The unit dose package, according to claim 12, which further comprises a second therapeutic agent for i.c. administration.

14. The unit dose package according to claim 12 wherein the $H_2$ agonist is Impromidine and is administered intracavernous in an amount from about 25 mcg to about 600 mcg.

15. The method according to claim 1 which further comprises administering with the $H_2$ receptor agonist a penetration enhancing agent.

16. The method according to claim 1, or 11 wherein the $H_2$ agonist is administered by intracavernosum injection.

17. The method according to claim 1, or 11 wherein the $H_2$ agonist is administered topically.

18. The method according to claim 1, or 11 wherein the $H_2$ agonist is administered intraurethrally.

19. Unit dose packaging for a single use topical administration, wherein said unit dose packaging contains an effective amount of a topical formulation of an $H_2$ receptor agonist that promotes erection.

20. Unit dose packaging for a single use intraurethral administration, wherein said unit dose packaging contains an effective amount of an intraurethral formulation of an $H_2$ receptor agonist that promotes erection.

21. Unit dose packaging according to claim 12 wherein said unit dose packaging contains an effective amount of from about 50 mcg to about 2,000 mcg of an $H_2$ receptor agonist that promotes erection.

22. Unit dose packaging according to claim 19 wherein said unit dose packaging contains an effective amount of from about 50 mcg to about 2,000 mcg of an $H_2$ receptor agonist that promotes erection.

23. Unit dose packaging according to claim 20 wherein said unit dose packaging contains an effective amount of from about 50 mcg to about 2,000 mcg of an $H_2$ receptor agonist that promotes erection.

24. The method according to claim 1 which method is applied to mammals in the veterinary sciences.

25. An intracavenosal composition which composition comprises an effective amount of an $H_2$ agonist which promotes erection, and a pharmaceutically acceptable carrier or diluent.

26. An intraurethral composition, which composition comprises an effective amount of an $H_2$ agonist which promotes erection, and a pharmaceutically acceptable carrier or diluent.

27. A method of treating female sexual dysfunction in a human in need thereof which method comprises administering to said human an effective amount of an $H_2$ agonist.

28. The method according to claim 27 wherein the $H_2$ agonist is a compound of the formula wherein

Het is a 4-imiazolyl, 5-methyl-4-imidazolyl, 5-ethyl-4-imidazolyl, 5-halogeno-4-imidazolyl, 2-thiazolyl, 3-isothiazolyl, 4-halogeno-3-isothiazolyl, 2-pyridyl, 3-methyl-2-pyridyl, 3-ethyl-2-pyridyl, 3-halogeno-2-pyridyl, 3-hydroxy-2-pyridyl, 3-methoxy-2-pyridyl or 3-ethoxy-2-pyridyl ring;

Het' is a 4-imidazole ring;

halogeno is bromo or chloro; or a hydrate or pharmaceutically acceptable salt or hydrated salt thereof.

29. The method according to claim 28 which is N-[3-(Imidazolyl)propyl]-N'-[2-(4-methyl-5-imidazolylmethylthio)ethyl]guanidine or a hydrate of pharmaceutically acceptable salt thereof.

30. The method according to claim 27 wherein the $H_2$ agonist is of the formula:

wherein $R_1$ and $R_2$ may be the same or different and are methyl or ethyl, or the pharmaceutically acceptable salts thereof.

31. The method according to claim 30 wherein the compound is (3-dimethyl-aminopropyl)isothiourea and pharmaceutically acceptable salts thereof.

32. The method according to claim 27 which further comprises a second therapeutic agent which either facilitates, potentiates or is erectogenic.

33. The method according to any of claim 27 to 32 which further comprises administering with the $H_2$ receptor agonist a penetration enhancing agent.

34. The method according to claims 27 wherein the $H_2$ agonist is further administered in combination with one or more therapeutically active agents which are an $H_3$ agonist, histamine, an α-adrenergic blocker, a dopamine $D_2$-antagonist, nitric oxide releaser, prostaglandin or an analog thereof having a vasoactive function, calcium antagonist, CGRP, VIP, phentolamine, physiostigmine, neostigmine, hydralazine, sodium nitroprusside, phenoxybenzamine, or an $H_1$ antagonist.

* * * * *